United States Patent [19]
Morishita et al.
[11] 3,960,757
[45] June 1, 1976

[54] PROCESS FOR ENCAPSULATION OF MEDICAMENTS

[75] Inventors: Masataka Morishita; Yoshihito Inaba; Mitsuru Fukushima; Yoshinori Hattori; Sadami Kobari; Tetsuo Matsuda, all of Shizuoka, Japan

[73] Assignee: Toyo Jozo Co., Ltd., Japan

[22] Filed: June 29, 1973

[21] Appl. No.: 375,027

[52] U.S. Cl. .................................. 252/316; 424/32; 424/33; 424/35; 424/38; 424/181; 424/242; 424/243; 424/244; 424/271; 424/299; 424/324; 427/3; 427/212

[51] Int. Cl.[2] ........................................... B01J 13/02

[58] Field of Search ....................... 252/316; 424/35; 117/100 A; 427/3, 212

[56] References Cited

UNITED STATES PATENTS

| | | | |
|---|---|---|---|
| 3,523,906 | 8/1970 | Vrancken et al. | 252/316 |
| 3,691,090 | 9/1972 | Kitajima et al. | 252/316 |
| 3,737,337 | 6/1973 | Schnoring et al. | 252/316 X |
| 3,784,391 | 1/1974 | Kruse et al. | 252/316 X |

*Primary Examiner*—Richard D. Lovering
*Attorney, Agent, or Firm*—Craig & Antonelli

[57] ABSTRACT

Encapsulated medicaments are prepared by dissolving a wall material for capsules in at least one organic solvent poorly miscible with water which has a boiling point of less than 100°C., a vapor pressure higher than that of water and a dielectric constant of less than about 10, dissolving or dispersing in the resulting solution a medicament which is insoluble or slightly soluble in water, dispersing the resulting solution or dispersion to the form of fine drops in a liquid vehicle comprising an aqueous solution of a hydrophilic colloid or surface active agent, and then removing the organic solvent by evaporation.

16 Claims, No Drawings

PROCESS FOR ENCAPSULATION OF MEDICAMENTS

This invention relates to a novel process for encapsulation of water-insoluble or slightly water-soluble medicaments according to evaporating method in liquid vehicle.

As processes for encapsulation of medicaments which belong to the category of evaporating method in liquid vehicle, there have heretofore been known processes carried out by emulsifying an aqueous solution of a core substance into a solution of a wall material for capsules in a water-immiscible organic solvent, further emulsifying the resulting emulsion into an aqueous solution to form a composite emulsion of the [(W/O)/W] type, and then removing the organic solvent by heating or by reduced pressure distillation (refer to Japanese Patent Publication Nos. 28,744/64, 13,703/67, 10,863/68 and 2,757/70). According to these processes, however, the core substance is always an aqueous solution or suspension so that the resulting microcapsules become hydrous. In view of stability of the microcapsules, therefore, the said processes have not been suitable for encapsulation of medicaments. The process disclosed in Japanese Patent Publication No. 9,836/71 is concerned with a process for encapsulation of aspirin by adoption of the evaporating method in liquid vehicle. In this process, however, a concentrated aqueous inorganic salt solution is used as the vehicle, and the core substance used is limited to a substance which can be salted out by said concentrated aqueous inorganic salt solution and which does not react with the inorganic salt in said aqueous solution. Accordingly, the said process has also been difficultly adopted for the encapsulation of medicaments.

An object of the present invention is to provide a process for encapsulating various water-insoluble or slightly water-soluble medicaments, regardless of the physical properties thereof.

Another object of the invention is to provide a process for preparing encapsulated medicaments in which a suitable wall material for capsules is selected so as to make them gastric soluble, enteric soluble gastric-enteric soluble or slow release.

A further object of the invention is to provide a process for preparing microcapsules of medicaments which have no foams.

A still further object of the invention is to provide a process for preparing microcapsules for medicaments which are excellent in water repellency to aqueous paste-like medicaments.

In accordance with the present invention, there has been found, in order to accomplish the above-mentioned objects, a process for preparing encapsulated medicaments which comprises dissolving or dispersing a water-insoluble or slightly water-soluble medicament into a solution of a hydrophobic wall material in at least one organic solvent poorly miscible with water which has a boiling point of not more than 100°C., a vapor pressure higher than that of water and a dielectric constant of not more than about 10, dispersing the resulting solution or dispersion to the form of fine drops in a vehicle, and then vaporizing the organic solvent. It has also been found that when two or more of such organic solvents as mentioned above are used in admixture, more fine and excellent encapsulated medicaments can be obtained. According to the process of the present invention, there are obtained microcapsules which contain substantially uniformly a water-insoluble or slightly water-soluble medicament and which are not hollow.

CORE SUBSTANCE

The medicament, which is used as a core substance in the present invention, is not particularly limited in kind so far as it is insoluble or slightly soluble in water. However, a medicament reactive with the wall material mentioned later is not usable. In case the medicament, i.e., the core substance, is soluble in an organic solvent, it may be used in the form of a solution in the organic solvent. In case the medicament is insoluble in an organic solvent, it may be pulverized to fine particles of preferably not more than 5 microns and used in the form of a dispersion in the organic solvent. Typical examples of water-insoluble and slightly water-soluble medicaments are as follows:

a. Medicaments soluble in organic solvents:

Kitasamycin, acetyl-kitasamycin, spiramycin, acetyl-spiramycin, estradiol, erthromycin, erythromycin ethyl succinate, cortisone acetate, hydrocortisone acetate, predomisolone acetate, diazepam, triacetyl oleandomycin, chloroamphenicol palmitate, phenacetin, progesterone, testosterone propionate, hexobarbital and methyl testosteron.

b. Medicaments insoluble in organic solvents:

Ampicillin trihydrate, chloramphenicol, chlorodiazepoxide, cyclobarbital, strychnine nitrate, dexamethazone, tetracycline, nalidixic acid, barbital, hydrocortisone, predonisolone, bromvalerylurea and folic acid.

SOLVENT

The organic solvent used in the present invention is an organic solvent that is poorly miscible, i.e. an organic solvent ranging from one which is entirely immiscible with, to one which is miscible in an amount of only about 10% with, the vehicle, comprising an aqueous solution of a hydrophilic colloid or surface active agent. Further, the organic solvent is required to have a dielectric constant of not more than about 10, a boiling point of not more than 100°C., preferably 40° to 80°C., and a vapor pressure of more than that of water. Examples of such organic solvents include ethyl ether, isopropyl ether, methylene chloride, ethylene chloride, chloroform, carbon tetrachloride, methyl acetate and ethyl acetate. Alternatively, a mixture of two or more organic solvents may be used. Preferably, the organic solvents used in admixture have a difference in boiling point of not less than 10°C. Examples of such mixed solvents include chloroform-methylene chloride, benzene-methylene chloride and ethylene chloride-methylene chloride.

WALL MATERIAL

The wall material used in the present invention to form wall films of microcapsules may be any material so far as it is hydrophobic and does not react with the aforesaid medicaments. Depending on the properties and application purpose of the medicament, which is the core substance to be contained in the microcapsules, the wall material is classifed into gastric soluble, enteric soluble and semipermeable materials. A wall material, which provides a proper viscosity when dissolved in the aforesaid organic solvent, is particularly suitable for preparation of microcapsules.

Examples of the gastric soluble wall material, which is a high molecular synthetic polymer, are cellulose acetate dibutylaminohydroxypropyl ether and polyvinyl acetal diethylamino acetate. An example of the gastric and enteric soluble wall material, which is a high molecular synthetic polymer, is a 2-methyl-5-vinylpyridine methacrylate-methacrylic acid copolymer. An example of the enteric soluble wall material, which is a high molecular synthetic polymer, is hydroxypropyl methyl cellulose phthalate. Examples of the semipermeable wall material, which is a high molecular synthetic polymer, are ethyl cellulose, cellulose acetate, cellulose propionate, cellulose butyrate, cellulose valerate, cellulose acetate propionate, polyvinyl acetate, polyvinyl formal, polyvinyl butyral, ladder polymer of sesquiphenyl siloxane, polymethyl methacrylate, polycarbonate, polystyrene, polyester, cumaroneindene polymer, polybutadiene, vinyl chloride-vinyl acetate copolymer, ethylene-vinyl acetate copolymer and vinyl chloride-propylene-vinyl acetate copolymer. Further, examples of natural wall materials, which are soluble at the duodenum and which soften at elevated temperatures, preferably at 50°C. or more, are waxes such as beef tallow, whale wax, bees wax, paraffin wax and castor wax, and higher fatty acids such as myristic, palmitic, stearic and behenic acids and esters thereof. The above-mentioned hydrophobic wall materials may be used in the form of a mixture of two or more. In order to enhance the water repellency of the resulting microcapsules, it is particularly preferable to use the aforesaid high molecular synthetic polymer in admixture with the above-mentioned wax or higher fatty acid.

VEHICLE

The vehicle used in the present invention is an aqueous solution of a hydrophilic colloid or surface active agent, in which an organic solvent solution of the said hydrophobic wall material containing medicament can be dispersed to the form of fine drops, and in which the said fine drops are stable. As the aqueous solution of hydrophilic colloid, there is used an aqueous solution containing 0.05 to 5% W/V, preferably 0.5 to 2% W/V, of gelatin, gelatin derivative, polyvinyl alcohol, polystyrene-sulfonic acid, hydroxymethyl cellulose, hydroxyethyl cellulose, hydroxypropyl cellulose, sodium carboxymethyl cellulose or sodium polyacrylate. As the aqueous solution of surface active agent, there is used an aqueous solution containing 0.01 to 2% W/V, preferably 0.1 to 1% W/V, of a water-soluble anionic or nonionic surface active agent having an HLB of not less than 10. Alternatively, a mixture of the aqueous solutions of hydrophilic colloid and surface active agent may also be used. In this case, it is preferable to use a 0.5 to 2% W/V aqueous solution of hydrophilic colloid in admixture with a 0.05 to 0.5% W/V aqueous solution of anionic surface active agent.

PROCESS OF ENCAPSULATION

In practicing the process of the present invention, a hydrophobic wall material is first dissolved in the aforesaid organic solvent. In this case, the concentration of the wall material varies depending on the kinds of the wall material and the organic solvent. If the concentration of the wall material solution is excessively high, the solution is difficultly dispersed in the vehicle, while if the concentration is excessively low, not only the dispersed droplets becomes unstable but also a long time is required for evaporation of the organic solvent. A suitable concentration is 0.5 to 20% W/V, preferably 2.5 to 10% W/V. The organic solvent may be incorporated with such suspension powder as talc, silicon dioxide, aluminum silicate, starch, dextrin, magnesium stearate, aluminum stearate, D-mannitol, titanium oxide, magnesium carbonate or aluminum hydroxide gel, whereby more stable fine drops can be formed when the wall material solution is dispersed into the aqueous solution of hydrophilic colloid or detergent. In the next place, a medicament, i.e., a core substance, is dissolved or uniformly dispersed in the organic solvent solution of wall material. In case the medicament is soluble in the organic solvent, it is used in the form of a solution in said organic solvent together with the wall material. At the time of evaporization of the organic solvent, therefore, a concentration gradient is observed in each of the resulting microcapsules due to the hydrophobic property of the medicament and the hydrophilic property of the wall material, and the density of the wall material is high at portions nearer to the exterior of the microcapsule while the density of the medicament is higher at portions nearer to the center of the microcapsule, with the result that there are obtained microcapsules in which no boundary is seen between the wall material and the medicament, i.e., the core substance. In case the medicament is insoluble or slightly soluble in the organic solvent, it is pulverized to a fine powder of preferably not more than 5 microns and then uniformly dispersed in the organic solvent solution of the wall material. In this case, therefore, there are obtained concrete-like microcapsules in which fine particles of the medicament have been embedded in the wall material. The amount of the medicament used may be optionally selected. Ordinarily, the medicament is used in an amount of not more than 2 times the dry weight of the wall material, whereby a solution or dispersion excellent in coating processability can be obtained. The solution or dispersion containing the medicament and the wall material is dispersed with stirring to the form of fine drops into 1 to 10 times, preferably 2 to 5 times, the amount of a vehicle. The size of the fine drops can be suitably decided according to the stirring speed, the viscosity of the organic solvent solution containing the medicament and the wall material, and the viscosity and surface tension of the vehicle. Subsequently, the dispersion containing the fine drops is allowed to stand at room temperature with stirring or is heated to evaporate the organic solvent, whereby the wall material deposits around the fine drops. Preferably, the dispersion is maintained at a temperature of at least 20°C. lower than the boiling point of the organic solvent to evaporate a part of the organic solvent until the concentration of the wall material in the fine drops becomes not less than 60% W/V, and then the organic solvent is completely removed at a maximum temperature of about 5°C. below the boiling point of the organic solvent to form microcapsules having excellent wall films which are high in density and contain no bubbles at all. Subsequently, the microcapsules are recovered, washed with water and then dried, whereby microcapsules containing the medicament can be obtained. In case one organic solvent is used, the fine drops for forming microcapsules are increased in viscosity at the time of evaporation of the organic solvent to cohere to one another, so that the resulting microcapsules become large in size and the surface thereof become markedly porous and coarse. In case two or more organic solvents are different in boiling point are used in the form of a mixture, however, the fine drops for forming microcapsules are present in a stable form in the high boiling solvent at the time of evaporation of the low boiling solvent and do not form lumps despite of their being high in viscosity, with the result that extremely fine microcapsules can be formed. Further, even when the low boiling point solvent contained in the fine drops has completely been evaporated, the microcapsule-forming fine drops provide markedly smooth and pinhole-free surfaces due to action of the high boiling point solvent. Accordingly, extremely fine microcapsules having smooth surfaces can be obtained by subsequent evaporation of the high boiling point solvent. One or more of the above-mentioned organic solvents may be incorporated with not more than 10% V/V, preferably 1 to 5% V/V, of acetone, ethanol, methanol or the like organic solvent which is miscible with the said solvents and with the aforesaid vehicle and which has a boiling point of not more than 100°C., preferably not more than 80°C., whereby the formation of pinholes and bubbles can be prevented.

According to the process of the present invention, the microcapsules are prepared under mild conditions, so that the medicament contained therein is not degraded in effectiveness. Further, the microcapsules are not only excellent in concealing the bitter taste or offensive odor of the medicament contained therein and in maintaining the stability and of effectiveness of the medicament but also are so fine as to be handled as a dust. Moreover, the microcapsules individually contain the medicament in an amount substantially identical therewith, and hence are very suitably used as a medicine.

The process of the present invention is illustrated in detail below with reference to examples, but the invention is not limited to the examples.

EXAMPLE 1

A solution of 4 g. of kitasamycin and 1 g. of ethyl cellulose in 20 ml. of methylene chloride was dispersed with stirring at 300 r.p.m. in 100 ml. of a 1% W/V aqueous gelatin solution. Subsequently, the stirring was continued at 18°C. for 60 minutes and then at 30°C. for 60 minutes to obtain 3.8 g. of kitasamycin-containing microcapsules of 140 to 300 microns in particle size. The thus obtained microcapsules had been enhanced in slow release of kitasamycin by the ethyl cellulose.

EXAMPLE 2

A solution of 4 g. of chloramphenicol and 1 g. of beef tallow in 25 ml. of ethyl acetate was dispersed with stirring at 400 r.p.m. in 100 ml. of a 1% W/V aqueous gelatin solution. Subsequently, the stirring was continued at room temperature for 2 hours to obtain 3.5 g. of microcapsules of 240 to 530 microns in particle size. The thus obtained microcapsules had been shielded from bitter taste of the chloramphenicol.

EXAMPLE 3

4 Grams of a fine powder (0.5 to 5 microns) of ampicillin trihydrate was dispersed in a solution of 1 g. of hydroxypropyl methyl cellulose phthalate ("HP-50" trade name, produced by Shin-etsu Chemical Co.) in 20 ml. of methylene chloride containing 0.5 ml. of acetone. The resulting dispersion was dispersed with stirring at 280 r.p.m. in 100 ml. of a 1% W/V aqueous gelatin solution. Subsequently, the stirring was continued at room temperature for 2 hours to obtain 3.7 g. of microcapsules of 700 to 1,200 microns in particle size. The thus obtained microcapsules were not inactivated even when used in combination with dichloxacillin of ampicillin trihydrate.

EXAMPLE 4

A solution of 4 g. of josamycin and 1 g. of ethyl cellulose in 40 ml. of ethyl ether was dispersed with stirring at 350 r.p.m. in 100 ml. of a 1% W/V aqueous gelatin solution. Subsequently, the stirring was continued at room temperature for 3.5 hours to obtain 3.8 g. of microcapsules of 40 to 150 microns in particle size.

EXAMPLE 5

A solution of 4 g. of kitasamycin and 1 g. of polyvinyl acetal diethylamino acetate ("AEA": trade name, produced by Sankyo Co.) in 40 ml. of a mixed organic solvent of chloroform-methylene chloride (1 : 1) was dispersed with stirring at 400 r.p.m. in 100 ml. of a 1% of W/V aqueous gelatin solution. Subsequently, the stirring was continued at room temperature for 5 hours to obtain 3.5 g. of microcapsules of 30 to 70 microns in particle size. The thus obtained microcapsules were so stable as not to be inactivated in fodder.

EXAMPLE 6

A solution of 4 g. of chloramphenicol palmitate, 2 g. of HP-50 and 2 g. of bees wax in 30 ml. of a mixed organic solvent of benzenemethylene chloride (1 : 2) was dispersed with stirring at 400 r.p.m. in 100 ml. of a 1% W/V aqueous gelatin solution. Subsequently, the stirring was continued at 45°C. for 4.5 hours to obtain 5.4 g. of microcapsules of 30 to 80 microns in particle size.

EXAMPLE 7

A solution of 4 g. of diazepam, 2 g. of ethyl cellulose and 2 g. of stearic acid in 40 ml. of a mixed organic solvent of ethylene chloride-methylene chloride (1 : 1) was dispersed with stirring at 400 r.p.m. in 100 ml. of a 1% W/V aqueous gelatin solution. Subsequently, the stirring was continued at room temperature for 2 hours and then at about 40°C. for 2.5 hours to obtain 3.6 g. of microcapsules of 30 to 60 microns in particle size. The thus obtained microcapsules could make the effectiveness of the diazepam persistent.

EXAMPLE 8

A solution of 19.4 kg. of kitasamycin and 2.6 kg. of AEA in 40 kg. of a mixed organic solvent of chloroform-methylene chloride (1 : 1) was dispersed with stirring at 100 r.p.m. in 120 liters of a 1.5% W/V aqueous gelatin solution containing 240 ml. of Tween 20. Subsequently, the stirring was continued at 25°C. for 48 hours to obtain 20.9 kg. of microcapsules of 150 to 500 microns in particle size.

EXAMPLE 9

0.5 Gram of talc was dispersed in a solution of 4 g. of erythromycin and 0.5 g. of polybutadiene in 30 ml. of benzene. The resulting dispersion was dispersed with stirring at 400 r.p.m. in 100 ml. of a 0.1% W/V aqueous sodium polyoxyethylene nonylphenyl ether butyl sulfonate solution. Subsequently, the stirring was continued at room temperature for 4.5 hours to obtain microcapsules of 50 to 150 microns in particle size.

EXAMPLE 10

A solution of 6 g. of kitasamycin, 2 g. of AEA and 2 g. of Lubri Wax 101 in 40 ml. of methylene chloride containing 2 ml. of ethanol was dispersed with stirring at 550 r.p.m. in 200 ml. of a 0.5% W/V aqueous sodium laurylbenzene-sulfonate. Subsequently, the stirring was continued at room temperature for 3 hours to obtain 7.7 g. of microcapsules of 10 to 50 microns in particle size.

EXAMPLE 11

A solution of 6 g. of kitasamycin, 2 g. of AEA and 2 g. of Lubri Wax 101 in 40 ml. of chloroform was dispersed with stirring at 600 r.p.m. in 200 ml. of a 0.5% W/V aqueous sodium laurylbenzene-sulfonate solution. Subsequently, the stirring was continued at room temperature for 3 hours to obtain 7.5 g. of microcapsules of 10 to 40 microns in particle size. The thus obtained microcapsules made it possible to stabilize the kitasamycin in the syrup and to easily absorb the same in the digestive tract.

EXAMPLE 12

A solution of 6 g. of spiramycin, 2 g. of AEA and 2 g. of Lubri Wax 101 in 40 ml. of a mixed organic solvent of chloroform-methylene chloride (1 : 2) was dispersed with stirring at 600 r.p.m. in 200 ml. of an aqueous solution containing 1 g. of sodium laurylbenzene-sulfonate and 2 g. of gelatin. Subsequently, the stirring was continued at room temperature for 3.5 hours to obtain 8.0 g. of microcapsules of 10 to 50 microns in particle size.

EXAMPLE 13

A solution of 6 g. of kitasamycin, 2 g. of AEA and 2 g. of stearic acid in 40 ml. of methylene chloride was dispersed with stirring at 600 r.p.m. in 200 ml. of an aqueous solution containing 1 g. of sodium laurylbenzene-sulfonate and 2 g. of gelatin. Subsequently, the stirring was continued at room temperature for 3 hours to obtain 7.8 g. of microcapsules of 10 to 50 microns in particle size.

EXAMPLE 14

2 Grams of finely divided hydrocortisone was dispersed in a solution of 2 g. of ethyl cellulose and 2 g. of stearic acid in 50 ml. of methylene chloride. The resulting dispersion was dispersed with stirring at 400 r.p.m. in 150 ml. of a 0.1% W/V aqueous gelatin solution kept at 10°C. Subsequently, the stirring was continued at 45°C. for 2 hours to obtain 4.3 g. of microcapsules of 100 to 300 microns in particle size. The thus obtained microcapsules could normalize the rapid degradation in effectiveness in living bodies of the hydrocortisone.

EXAMPLE 15

2 Grams of finely divided progesterone was dissolved in 50 ml. of a mixed organic solvent of methylene chloride-chloroform (1 : 1) containing 2 g. of cellulose acetate and 2 g. of palmitic acid. The resulting solution was dispersed with stirring at 450 r.p.m. in 300 ml. of a 1% W/V aqueous gelatin solution kept at 20°C. Subsequently, the stirring was continued at 40°C. for 3.5 hours to obtain 3.9 g. of microcapsules of 20 to 50 microns in particle size.

What is claimed is:

1. A process for preparing encapsulated medicines, characterized by dissolving a gastric-soluble, enteric soluble or semipermeable hydrophobic wall material in at least one organic solvent immiscible with water which has a boiling point of not more than 100°C., a vapor pressure higher than that of water and a dielectric constant of not more than 10, dissolving or dispersing in the resulting solution a water-insoluble or slightly water-soluble medicament, dispersing the resulting solution or dispersion to the form of fine drops into a vehicle consisting of a hydrophilic colloid or a surface active agent in water, and then evaporating the organic solvent.

2. A process according to claim 1, wherein the organic solvent has a boiling point of 40° to 80°C. and a solubility in water of not more than 10% V/V.

3. A process according to claim 1, wherein the hydrophobic wall material is a mixture of a non-toxic and gastric soluble, enteric soluble or gastric-enteric soluble high molecular weight synthetic polymer with a non-toxic wax or higher fatty acid or an ester thereof which has a melting point of not less than 50°C.

4. A process according to claim 1, wherein the medicament used as the core substance in an organic solvent-insoluble medicament having a particle size of not more than 5 microns.

5. A process according to claim 1, wherein the vehicle is a 0.5 to 20% W/V aqueous hydrophilic colloid solution.

6. A process according to claim 1, wherein the vehicle is a 0.1 to 1% W/V aqueous anionic surface active agent solution having an HLB of not less than 10.

7. A process according to claim 1, wherein the vehicle is a mixture of 0.5 to 2% W/V aqueous hydrophilic colloid solution with a 0.05 to 0.5% W/V aqueous anionic surface active agent solution having an HLB of not less than 10.

8. A process according to claim 1, wherein content of the medicament in microcapsule is not more than 66% W/W; the hydrophobic wall material is used at a concentration of 5 to 10% W/V; the medicament is used in not more than 2 times the amount of hydrophobic wall material; and the vehicle is used in 2 to 5 times the amount of the organic solvent containing the medicament and the hydrophobic wall material.

9. A process according to claim 1, wherein said hydrophobic wall material is dissolved in a mixture of at least two organic solvents.

10. A process according to claim 9, wherein the difference between boiling points between the organic solvents is not less than 10°C.

11. A process according to claim 1, wherein the solution of the hydrophobic wall material in the water-immiscible organic solvent further contains a miscible organic solvent miscible with said vehicle and miscible with said water-immiscible organic solvent, said miscible organic solvent having a boiling point of no more than 100°C.

12. A process according to claim 11, wherein said solution contains no more than 10% V/V of sad miscible organic solvent.

13. A process according to clailm 1, wherein said medicament is dissolved in said resulting solution.

14. A process according to claim 1, wherein said hydrophobic wall material does not react with said medicament.

15. A process according to claim 1, wherein said vehicle consists essentially of 0.5 to 20% W/V aqueous hydrophilic colloid solution or 0.1 to 1% W/V aqueous anionic surface active agent solution having an HLB of not less than 10.

16. A process for preparing water repellent encapsulated medicines, which comprises dissolving a mixture of a polymer selected from the group consisting of cellulose acetate dibutylaminohydroxypropyl ether, polyvinyl acetal diethylamino acetate, 2-methyl-5-vinylpyridine methacrylate-methacrylic acid copolymer, hydroxypropyl methyl cellulose phthalate, ethyl cellulose, cellulose acetate, cellulose propionate, cellulose butyrate, cellulose valerate, cellulose acetate propionate, polyvinyl acetate, polyvinyl formal, polyvinyl butyral, ladder polymer of sesquiphenyl siloxane, polymethyl methacrylate, polycarbonate, polystyrene, polyester, cumarone-indene polymer, polybutadiene, ethylene-vinyl acetate copolymer and vinyl chloride-propylene-vinyl acetate copolymer with a non-toxic wax or a higher fatty acid or an ester thereof having a melting point of not less than 50°C in at least one organic solvent immiscible with water which has a boiling point of not more than 100°C, a vapor pressure higher than that of water and a dielectric constant of not more than 10, dissolving or dispersing in the resulting solution a medicament selected from the group consisting of kitasamycin, acetyl-kitasamycin, spiramycin, acetylspiramycin, estradiol, erythromycin, erythromycin ethyl succinate, cortisone acetate, hydrocortisone acetate, predomisolone acetate, diazepam, triacetyl oleandomycin, chloramphenicol palmitate, phenacetin, progesterone, testosterone propionate, hexobarbital, methyl testosteron, ampicillin trihydrate, chloramphenicol, chlorodiazepoxide, cyclobarbital, strychnine nitrate, dexamethazone, tetracycline, nalidixic acid, barbital, hydrocortisone, predonisolone, bromvalerylurea and folic acid, dispersing the resulting solution or dispersion in the form of fine drops into a vehicle consisting of a hydrophilic colloid or a surface active agent in water, and then evaporating the solvent.

* * * * *